United States Patent [19]

Kleemann et al.

[11] 4,374,062
[45] Feb. 15, 1983

[54] PROCESS FOR THE PRODUCTION OF PEPTIDES

[75] Inventors: Axel Kleemann, Hanau; Jurgen Martens, Alzenau; Marc Samson, Hanau, all of Fed. Rep. of Germany

[73] Assignee: Degussa Aktiengesellschaft, Frankfurt, Fed. Rep. of Germany

[21] Appl. No.: 311,454

[22] Filed: Oct. 14, 1981

[30] Foreign Application Priority Data

Oct. 16, 1980 [DE] Fed. Rep. of Germany ....... 3039053

[51] Int. Cl.$^3$ ............................................ C07C 103/52
[52] U.S. Cl. ............................................ 260/112.5 R
[58] Field of Search ................................ 260/112.5 R

[56] References Cited

PUBLICATIONS

M. Nakayama, et al., Bull. Chem. Soc., Japan 44, 1150–1152–(1971).
D. Meyer, et al., J. Org. Chem. 1980, 45, 4680–4682.
I. Ojima, et al., J. Org. Chem. 1982, 47, 1329–1334.
K. Onuma, et al., The Chem. Soc. of Japan, (1980), 481–482.
Chem. Abstr. 82, (1975), p. 97594a from Diss. Abstr. Int. B. 1974, 35 (6), 2660.
Chem. Abstr. 96, (1982), p. 20443g.
Chem. Abstr. 90, (1979), p. 23636j.
Chem. Abstr. 87, (1977), p. 5547q.
Chem. Abstr. 88, (1978), p. 121689g.
Chem. Abstr. 93, (1980), p. 114950k.
Ojima, Tetrahedron Letters, vol. 21, pp. 1239–1242, (1980).
Cahill, J. Biol. Chem., vol. 132, pp. 161–169, (1940).

Primary Examiner—Delbert R. Phillips
Attorney, Agent, or Firm—Cushman, Darby & Cushman

[57] ABSTRACT

There are produced peptides by asymmetrical hydrogenation of dehydropeptides of the general formula

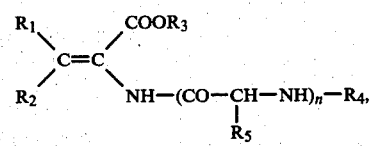

in which n is a whole number from 1 to 4, $R_1$ and $R_2$ are the same or different, and are hydrogen, a straight or branched chain alkyl group with 1 to 10 carbon atoms, or such a group substituted with a carboxyl group, a phenyl group which is unsubstituted or substituted in the 3 or 4 position or in both the 3 and 4 positions by a hydroxyl, alkoxy, or acyloxy group or an indolyl group which is unsubstituted or substituted in the 6 position by fluorine or chlorine or an indolyl group substituted by a methyl group. $R_3$ is hydrogen, an alkali metal, or a lower alkyl group with 1 to 4 carbon atoms, $R_4$ is hydrogen, an acetyl group or a chloroacetyl group and $R_5$ is hydrogen or a straight or branched chain alkyl group having 1 to 4 carbon atoms with the proviso that when n is 2, 3, or 4, the individual groups $R_5$ are the same or different, in the presence of chiral rhodium-complexes.

10 Claims, No Drawings

PROCESS FOR THE PRODUCTION OF PEPTIDES

BACKGROUND OF THE INVENTION

The present invention is directed to a process for the production of peptides by asymetrical hydrogenation of dehydropeptides in the presence of chiral rhodium complexes.

It is already known to produce peptides by asymmetrical hydrogenation of dehydropeptides of the general formula

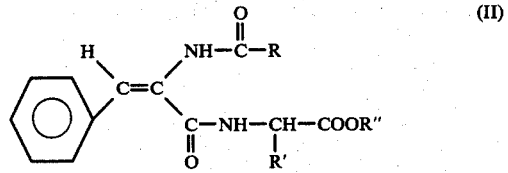

in which R is a methyl or phenyl group, R' is an alkyl or phenyl group and R" is hydrogen or an alkyl group in the presence of chiral rhodium complexes (Ojima, Tetrahedron Letters, Vol. 21, pages 1239 to 1242 (1980); Onuma, Chemistry Letters, 1980, pages 481 to 482). (The entire disclosure of both the Ojima and Onuma articles are hereby incorporated by reference and relied upon). In all the dehydropeptides employed the prochiral olefinic double bond is in the part of the molecule terminated with an amino group.

SUMMARY OF THE INVENTION

The process of the invention is characterized by employing for the hydrogenation dehydropeptides of the general formula:

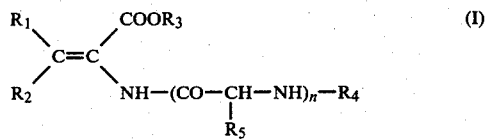

in which n is a whole number from 1 to 4, $R_1$ and $R_2$ are the same or different and are hydrogen, a straight or branched chain alkyl group with 1 to 10 carbon atoms, e.g. methyl, ethyl, propyl, isopropyl, butyl, sec.butyl, amyl, hexyl, octyl, isooctyl, decyl, or such a group substituted with a carboxyl group, a phenyl group which is unsubstituted or substituted in the 3 or 4 or in both the 3 and 4 positions by a hydroxyl, alkoxy, e.g., methoxy, ethoxy, butoxy, or acyloxy group, e.g., acetyl, propionyl, butyryl or an indolyl group which is unsubstituted or substituted in the 6 position by fluorine or chlorine or an indolyl group substituted by a methyl group, e.g., N-methyl, 2-methyl, 6-methyl, $R_3$ is hydrogen, an alkali metal, e.g. sodium, potassium, lithium or a lower alkyl group with 1 to 4 carbon atoms, e.g., methyl, ethyl, propyl, isopropyl, butyl, $R_4$ is hydrogen, an acetyl group or an chloroacetyl group and $R_5$ is hydrogen or a straight or branched chain alkyl group having 1 to 4 carbon atoms, e.g., methyl, ethyl, propyl, isopropyl, butyl, sec.butyl with the proviso that when n is 2, 3, or 4 the individual groups $R_5$ are the same or different. The hydrogenation is carried out in the presence of chiral rhodium-complexes. Thus there can be used for example, any of the chiral rhodium-complexes with chiral tertiary phosphines set forth in the above-identified Ojima and Onuma articles.

The dehydropeptides employed for the hydrogenation according to the process of the invention can already contain one or more asymmetric carbon atoms and in this case are used either in the form of the racemate or in the form of the optically active enantiomers. In each case in the asymmetrical hydrogenation there is introduced a new center of asymmetry, namely always in the part of the molecule terminated with a carboxyl group.

The dehydropeptide for hydrogenation is employed with a free carboxyl group, as alkali metal salt or as ester with an alkanol having 1 to 4 preferably 1 to 2, carbon atoms. There are hydrogenated with particularly good results in the process of the invention those dehydropeptides wherein in the above general formula (I) n is 1 or 2. As $R_4$ there are preferred acetyl or chloroacetyl.

Examples of hydrogenizable dehydropeptides according to the process of the invention are glycyl-dehydroleucine, N-acetyl-glycyl-dehydroleucine, N-chloroacetyl-glycyl-dehydroleucine, glycyl-dehydrophenylalanine, N-acetyl-glycyl-dehydrophenylalanine, N-chloroacetyl-glycyl-dehydrophenylalanine, glycyl-glycyl-dehydroalanine, N-acetyl-glycyl-dehydroalanine, N-chloroacetyl-glycyl-dehydroalanine, N-acetyl-glycyl-glycyl-dehydroleucine, N-acetyl-glycyl-glycyl-dehydrophenylalanine, N-chloro-acetyl-alanyl-dehydroalanine, N-chloroacetyl-glycyl-dehydrotryptophane, N-acetyl-glycyl-dehydrotryptophane, N-acetyl-glycyl-dehydroisoleucine, N-acetyl-glycyl-dehydrotyrosine, N-acetyl-glycyl-dehydroglutamic acid, N-chloroacetyl-glycyl-dehydrotyrosine, glycyl-dehydrotryptophane, glycyl-dehydroglutamic acid or glycyl-dehydrotyrosine.

For example the dehydropeptides employed can be produced in such manner that in the simplest case of the glycyl-dehydroaminoacids for which in formula (I) $n=1$ and $R_5=H$, an aminoacid is acylated with dichloroacetyl chloride, the N-dichloroacetyl aminoacid formed converted by means of a carboxylic anhydride, preferably acetic anhydride, into the corresponding 4-alkylidene or 4-arylalkylidene-2-chloromethyl-oxazolone, this is hydrolyzed to the corresponding N-chloroacetyl dehydroaminoacid and the latter reacted with ammonia to the corresponding glycyl-dehydroaminoacid. The latter can then be reacted again in the simplest case with chloroacetyl chloride to the corresponding N-chloroacetyl-glycyl-dehydroaminoacid and converted with ammonia into the corresponding glycyl-glycyl-dehydroamino acid, for which in formula (I) n is 2 and $R_5$ is H. The single or double repetition of the two last mentioned reaction steps then leads finally to dehydropeptides for which in formula (I) n is 3 or 4 and $R_5$ is H. If instead of starting from an amino acid and dichloroacetyl chloride there is employed an $\alpha,\alpha$-dichloroacyl chloride having 3 to 6 carbon atoms, e.g., an $\alpha,\alpha$-dichloroalkanoyl chloride such as $\alpha,\alpha$-dichloropropionyl chloride, $\alpha,\alpha$-dichlorovaleroyl chloride, $\alpha,\alpha$-dichlorobutyryl chloride, or $\alpha,\alpha$-dichlorocaproyl chloride and/or instead of chloroacetyl chloride there is used a higher $\alpha$-chloroacyl chloride having 3 to 6 carbon atoms, e.g. an $\alpha$-chloroalkanoyl chloride such as $\alpha$-chlorobutyryl chloride, $\alpha$-chloropropionyl chloride, $\alpha$-chlorovaleroyl chloride, or $\alpha$-chlorocaproyl chloride, then in the same way there can be produced corresponding dehydropeptides in which formula (I) $R_5$ is an alkyl group having 1 to 4 carbon atoms. The terminal group of the dehydropeptide in each case can then finally be acylated with acetic anhydride, acetyl chloride, or chloroacetyl chloride and/or the free carboxyl group can then be changed into an alkali metal salt, e.g. by reaction with sodium hydroxide or potassium hydroxide, or the carboxyl group can be changed into an ester group by reaction with an esterifying agent, e.g. an alkanol such as ethanol, methanol, or butanol.

The asymmetrical hydrogenation of the dehydropeptide takes place in the presence of soluble coordination complexes of a rhodium (I) compound and a chiral tertiary phosphine. This type of complex can be produced in situ by the reaction of a chiral tertiary phosphine with a complex of the general formula:

[Rh(en)$_2$X]$_2$, in which (en)$_2$ is two molecules of a monoolefin or cycloolefin (e.g. ethylene, butylene, octene-1, cyclooctene) or diolefin or cyclodiolefin (e.g. butadiene, isoprene, hexadiene-1,3, cyclooctadiene-1,5,norbornadiene) and X is chlorine, bromine, or iodine or with a complex of the general formula

[Rh(en)$_2$Y], in which (en)$_2$ is as defined above and Y is an acetonyl acetonate or a carboxylate group, e.g., an acetate, propionate, or butyrate group.

As catalysts for the asymmetrical hydrogenation finally there are also usable cationic complexes of the general formula

[Rh(en)$_2$A]$^+$Z$^-$ in which (en)$_2$ is as defined above, A is a chiral, tertiary phosphine and Z is a tetrafluoroborate, tetraphenylborate, hexafluorophosphate, or perchlorate anion.

A "chiral tertiary phosphine" denotes either a phosphine whose phosphorus atom has attached thereto three different hydrocarbon groups which in a given case can be substituted, or a phosphine which carries three hydrocarbon groups, that in a given case can be substituted, and at least one of the hydrocarbon (or substituted hydrocarbon) groups is a chiral group. Examples of such chiral tertiary phosphines are (+)-2,3-0-isopropylidene-2,3-dihydroxy-1,4-bis-(diphenylphosphino)-butane, (−)-1,2-bis-(0-anisylphenylphosphino)-ethane, (−)-(2R,3R)-bis-(diphenylphosphino)-bicylclo-[2.2.1]-hept-5-ene, (S)-(α)-[(R)-1′,2′-bis-(diphenylphosphino)-ferrocenyl]-ethyldimethylamine, (S,S)-N,N′-bis-(S)-α-methyl-benzyl-N,N′-bis-(diphenylphosphino)-ethane, (2S,4S)-N-butoxycarbonyl-4-diphenylphosphino-2-diphenylphosphino-methylpyrrolidine, (R)-1,2-bis-(diphenylphosphinomethyl)-cyclobutane, (R)-(+)-methylpropyl-o-dimethylaminophenylphosphine, (+)- and (−)-neomenthyl-diphenylphosphine, (S)-(+)- and (S)-(−)-1,2-bis-(diphenylphosphino)-1-phenylethane, (2R,4R)-bis-(diphenylphosphinomethyl)-dioxolane, (1R,2R)-bis-(N-diphenylphosphinomethylamino)cyclohexane, (1R,2R)-bis-(N-diphenylphosphinoamino)-cyclohexane, (S)-(−)-2,2′-bis-(diphenylphosphinomethyl)-1,1′-bis-naphthyl, (S,S)-2,3-bis-(diphenylphosphino)-butane, (R)-1,2-bis-(diphenylphosphino)-propane, 6-(S)-cyano-5-(R)-diphenylphosphino-(3R,4S)-O-isopropylidene-2-oxabicyclo-[3,2,0]-heptane.

The asymmetrical hydrogenation is carried out in the solvents customarily employed for hydrogenations such as alcohols, e.g., ethanol, methanol, isopropanol, or butanol and ethers, e.g., diethyl ether, dibutyl ether, dioxane, or their mixtures with aliphatic or aromatic hydrocarbons, e.g., hexane, decane, benzene, toluene, xylene, or in water. There also can be used mixtures of alcohols and water.

The concentration of the dehydropeptide to be hydrogenated can extend from a 0.001 molar up to a supersaturated solution of the dehydropeptides in question. The hydrogen pressure can be between normal (atmospheric) pressure and about 100 bar, preferably between normal pressure and 25 bar, the reaction temperature can be between −20° C. and +50° C. Preferably the hydrogenation is carried out at room temperature.

The chiral rhodium complexes are suitably employed in such amounts that the molar ratio of dehydropeptide to catalyst is in the range between 1:1 and 50,000:1, preferably between 100:1 and 5,000:1.

The peptides produced by the process of the invention serve as pharmaceuticals or as intermediate products for building higher peptides.

Unless otherwise indicated all parts and percentages are by weight.

The process can comprise or consist essentially of the steps recited with the stated materials.

The process of the invention is explained in more detail in the folowing examples which are not intended to limit the scope of the invention. The optical yield specified in the examples is defined as follows:

Optical Yield (%) =

$$\frac{\text{Measured optical activity of the mixture obtained}}{\text{Optical activity of the pure enantiomorph}} \times 100$$

DETAILED DESCRIPTION

EXAMPLE 1

3.7 grams of N-acetyl-glycyl-dehydroleucine were suspended in 50 ml of air free ethanol. To this suspension there were added 50 ml of an ethanolic solution which contained per ml 5.6 mg of [Rh(COD)-(+)-DIOP]BF$_4$, [(+)-DIOP stand for (+)-2,3-0-isopropylidene-2,3-dihydroxy-1,4-bis-(diphenylphosphino)-butane and (COD) for cyclooctadiene-1,5].

The mixture was shaken at 25° C. for 8 hours under hydrogen whereby the hydrogen pressure dropped from an initial 10 bars to 6.9 bar. Subsequently the reaction vessel was ventilated and the solvent removed under reduced pressure. As the residue there remained in the form of white crystals in nearly quantitative yield crude N-acetylglycyl-leucine having a specific rotation $[\alpha]_D^{25}$ of −6.7° (c=1; H$_2$O). (C=1 indicates a concentration of 1%). With a maximum rotary value $[\alpha]_D^{25}$ of −25.3° [Cahill, J. Biol. Chem. Vol. 132, pages 161–169, specifically 167 (1940)] this corresponds to an optical yield of 27% with (S)-configuration.

EXAMPLE 2

2.35 grams of N-acetyl-glycyl-dehydroleucine were dissolved in 50 ml of air free ethanol and treated with 5.0 ml of an ethanolic solution which contained per ml 4 mg of [Rh(COD)-(−)-BPPM]BF$_4$ [(−)-BPPM stands for (2S, 4S)-N-butoxycarbonyl-4-diphenyl-phosphino-2-diphenylphosphinomethyl-pyrrolidine].

The solution was shaken at 25° C. for 8 hours under hydrogen whereby the hydrogen pressure dropped from an initial 12.5 bar to 8.7 bar. Subsequently the reaction vessel was ventilated and the solvent removed under reduced pressure. There remained as residue in the form of a white crystal mass in nearly quantitative yield crude N-acetyl-glycylleucine having a specific rotation $[\alpha]_D^{25}$ of $+14.7°$ (c=1; H$_2$O). This corresponds to an optical yield of 58% with (R)-configuration.

EXAMPLE 3

2.8 grams of N-acetyl-glycyl-dehydroleucine were dissolved in 50 ml of air free ethanol and treated with 5.0 ml of an ethanolic solution which contained per ml 3.5 mg of [Rh (COD)-(R,R-2)]BF$_4$ [(R,R-2) stands for (1R,2R)-bis(diphenylphosphinoamino)-cyclohexane].

The solution was shaken at 25° C. for 8 hours under hydrogen, whereby the hydrogen pressure dropped from an initial 11 bar to 7.3 bar. Subsequently the reaction vessel was ventilated and the solvent removed under reduced pressure. As residue there remained in the form of a white crystal mass in practically quantitative yield crude N-acetylglycyl-leucine having a specific rotation $[\alpha]_D^{25}$ of $+9.5°$ (c=1; H$_2$O). This corresponds to an optical yield of 37.5% with (R)-configuration.

EXAMPLES 4 TO 6

Analogous to Examples 1 to 3 in each case there was hydrogenated 1.4 grams of N-chloroacetyl-glycyl-dehydroleucine. The reaction conditions and results are collected in Table I.

TABLE I

| Substrate | Product | Catalyst | H$_2$ Pressure (Bar) | $[\alpha]_D^{25}$ |
|---|---|---|---|---|
| N—Chloro-acetyl-glycyl-dehydro-leucine | N—Chloro-acetyl-glycyl-leucine | A | 10 | $-6.0°$ |
|  |  | B | 12 | $+13.8°$ |
|  |  | C | 20 | $+10.4°$ |

A: [Rh(COD)-(+)-DIOP]BF$_4$
B: [Rh(COD)-(−)-BPPM]BF$_4$
C: [Rh(COD)-(R,R-2)]BF$_4$
$[\alpha]_D^{25}$: measured in EtOH (c = 1)

EXAMPLES 7 TO 9

In each case 4.0 grams of degassed N-acetyl-glycyl-dehydrophenylalanine were suspended in 75 ml ethanol and treated with 5.0 ml of an ethanolic solution which contained per ml 4 mg of catalyst. The hydrogenation was undertaken at 25° C. After the end of the reaction time in each case the reaction vessel was ventilated and the solvent removed under reduce pressure. In all cases there remained in the form of a white crystal mass in practically quantitative yield crude N-acetyl-glycyl-phenylalanine. The reaction conditions and results are collected in Table II

TABLE II

| Catalyst | H$_2$ Pressure (Bar) | Reaction time (h) | $[\alpha]_D^{25}$ | Optical Yield | Configuration |
|---|---|---|---|---|---|
| A | 20 | 17 | $+19.5°$ | 43.3% | (S) |
| B | 15 | 14 | $-27.7°$ | 63% | (R) |

TABLE II-continued

| Catalyst | H$_2$ Pressure (Bar) | Reaction time (h) | $[\alpha]_D^{25}$ | Optical Yield | Configuration |
|---|---|---|---|---|---|
| C | 25 | 24 | $-17.3°$ | 39.3% | (R) |

A: [Rh(COD)-(+)-DIOP]BF$_4$
B: [Rh(COD)-(−)-BPPM]BF$_4$
C: [Rh(COD)-(R,R-2)]BF$_4$
$[\alpha]_D^{25}$: Measured in EtOH (c = 2) [Maximal Rotation Value: +44° (c = 2, EtOH) J.Chem.Soc. (C), 1967, 595–601]

EXAMPLES 10 TO 12

Analogous to Examples 7 to 9 in each case 4.3 grams of N-chloroacetyl-glycyl-dehydrophenylalanine were hydrogenated. The reaction conditions and results are collected in the following Table III.

| Catalyst | H$_2$ Pressure (bar) | Reaction time (h) | $[\alpha]_D^{25}$ | Probable Configuration |
|---|---|---|---|---|
| A | 15 | 18 | $+18.5°$ | (S) |
| B | 20 | 10 | $-23.3°$ | (R) |
| C | 15 | 24 | $-14.2°$ | (R) |

A: [Rh(COD)-(+)-DIOP]BF$_4$
B: [Rh(COD)-(−)-BPPM]BF$_4$
C: [Rh(COD)-(R,R-2)]BF$_4$
$[\alpha]_D^{25}$: measured in EtOH (c = 1)

The entire disclosure of German priority application No. P 3039053.5-42 is hereby incorporated by reference.

What is claimed is:

1. A process of producing peptides comprising asymmetrically hydrogenating a dehydropeptide of the formula

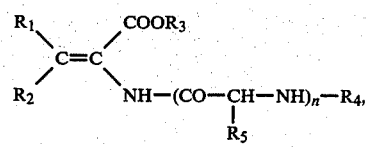

in which n is a whole number from 1 to 4, R$_1$ and R$_2$ are the same or different and are hydrogen, an alkyl group with 1 to 10 carbon atoms, or such a group substituted with a carboxyl group, a phenyl group which is unsubstituted or substituted in the 3 or 4 or in both the 3 and 4 positions by a hydroxyl, alkoxy, or acyloxy group or an indolyl which is unsubstituted or substituted in the 6 position by fluorine or chlorine or an indolyl group substituted by a methyl group, R$_3$ is hydrogen, an alkali metal, or a lower alkyl group with 1 to 4 carbon atoms, R$_4$ is hydrogen, an acetyl group or a chloroacetyl group and R$_5$ is hydrogen or an alkyl group having 1 to 4 carbon atoms with the proviso that when n is 2, 3, or 4, the individual groups R$_5$ are the same or different, in the presence of a chiral rhodium-complex which is either (1) a soluble coordination complex of a rhodium (I) compound and a chiral tertiary phosphine prepared by reaction of a chiral tertiary phosphine with (a) a complex of the formula

[Rh(en)$_2$X]$_2$, wherein (en)2 is two molecules of an olefin or cycloolefin or 1 mole of a diolefin or cyclodiolefin and X is chlorine, bromine, or iodine, or (b) with a complex of the formula

[Rh(en)₂Y], where Y is acetonylacetonate or a carboxylate group or (2) a cationic complex of the formula:

[Rh(en)₂A]⁺Z⁻ where A is a chiral, tertiary phosphine, and Z is a tetrafluoroborate, tetraphenyl borate, hexafluorophosphate, or perchlorate anion.

2. A process according to claim 1 where n is 1 or 2.

3. A process according to claim 2 where $R_1$ is hydrogen or methyl and $R_2$ is hydrogen, alkyl of 1 to 3 carbon atoms, phenyl, 4-hydroxyphenyl, carboxymethyl, or indolyl.

4. A process according to claim 3 where $R_5$ is hydrogen.

5. A process according to claim 4 where $R_3$ is hydrogen.

6. A process according to claim 5 where the compound of formula I is N-acetyl-glycyl-dehydroleucine.

7. A process according to claim 5 where the compound of formula I is N-chloroacetyl-glycyl-dehydroleucine.

8. A process according to claim 5 where the compound of formula I is N-acetyl-glycyl-dehydrophenylalanine.

9. A process according to claim 5 where the compound of formula I is N-chloroacetyl-glycyl-dehydrophenylalanine.

10. A process according to claim 5 wherein the compound of formula I is N-acetyl-glycyl-dehydroleucine, N-chloroacetyl-glycyl-dehydroleucine, N-acetyl-glycyl-dehydrophenylalnine or N-chloroacetyl-glycyl-dehydrophenylalanine.

* * * * *